United States Patent [19]

Gante et al.

[11] 3,948,949

[45] Apr. 6, 1976

[54] XANTHENE DERIVATIVES AND PROCESS FOR THE PREPARATION THEREOF

[75] Inventors: Joachim Gante; Hans-Adolf Kurmeier; Albrecht Wild; Werner Mehrhof, all of Darmstadt, Germany

[73] Assignee: Merck Patent Gesellschaft mit beschrankter Haftung, Darmstadt, Germany

[22] Filed: Jan. 28, 1974

[21] Appl. No.: 436,849

[30] Foreign Application Priority Data
Feb. 1, 1973   Germany............................ 2304763

[52] U.S. Cl................................. 260/335; 424/283
[51] Int. Cl.².............. C07D 311/82; C07D 311/84

[58] Field of Search..................................... 260/335

[56] References Cited
UNITED STATES PATENTS
3,639,612    2/1972    DeLong et al...................... 424/276

*Primary Examiner*—Norma S. Milestone
*Attorney, Agent, or Firm*—Millen, Raptes & White

[57] ABSTRACT

Xanthenes of the formula $Z\text{-}CHR_1R_2$ wherein Z is 2-xanthenyl or 2-xanthenyl substituted at the 1-, 3-, 4-, 5-, 6-, 7- or 8-position by F, Cl or Br, $R_1$ is $CH_2OH$ or $CH_2OAc$ wherein Ac is alkanoyl of 2–4 carbon atoms, and $R_2$ is H or alkyl of 1–4 carbon atoms, have antiphlogistic activity.

9 Claims, No Drawings

XANTHENE DERIVATIVES AND PROCESS FOR THE PREPARATION THEREOF

BACKGROUND OF THE INVENTION

This invention relates to novel xanthenes.

SUMMARY OF THE INVENTION

The xanthenes of this invention are those of the general Formula I $$Z\text{-}CHR_1R_2 \qquad \qquad I$$

wherein Z is unsubstituted 2-xanthenyl or 2-xanthenyl substituted in the 1-, 3-, 4-, 5-, 6-, 7- or 8-position by $R_3$, wherein $R_3$ is F, Cl or Br, $R_1$ is $CH_2OH$ or $CH_2OAc$, wherein Ac is alkanoyl of 2–4 carbon atoms, and $R_2$ is H or alkyl of 1–4 carbon atoms.

Compounds of Formula I possess with good compatibility excellent antiphlogistic activity and have a particularly favorable effect on the chronically progressing pathological processes at the joints. They also possess analgesic and antipyretic activity.

The compounds of Formula I can, therefore, be employed as drugs, especially for obtaining antiphlogistic effects in living beings, and also as intermediates for the production of other medicines.

DETAILED DISCUSSION

Of the compounds of Formula I, preferred are those wherein:

a. Z is unsubstituted 2-xanthenyl;
b. $R_1$ is $CH_2OH$, especially those of (a);
c. $R_2$ is H, $CH_3$ or $C_2H_5$, preferably $CH_3$, especially those of (a) and (b);
d. Z is substituted by Cl, i.e., $R_3$ is Cl, especially those of (b) and (c);
e. $R_1$ is $CH_2OAc$ and Ac, which can be acetyl, propionyl, butyryl, or isobutyryl, is preferably acetyl, especially those of (a), (c) and (d).

In its process aspect, this invention relates to processes for the production of compounds of the general Formula I wherein A. a compound of the general Formula II $$Z\text{--}X \qquad \qquad II$$

wherein X, which is a group convertible into the group $-CHR_1R_2$ and Z, $R_1$, $R_2$ and $R_3$ have the values given in Formula I, is converted into the group $-CHR_1R_2$; or B. a compound of the general Formula III

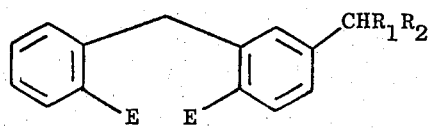

III wherein one of the E groups is the group $E_1$ and the other is $O\text{-}E_2$, in which $E_1$ is a group which can be split off together with $E_2$ as $E_1E_2$, and $E_2$ is H or an equivalent of an alkali or alkaline earth metal, or the corresponding compound in which one of the two benzene rings is substituted by $R_3$ at a position other than that bearing the $-CHR_1R_2$ group, and $R_1$, $R_2$ and $R_3$ have the values given in Formula I, is treated with an agent which splits off $E_1$-$E_2$; or C. a compound of the general Formula IV

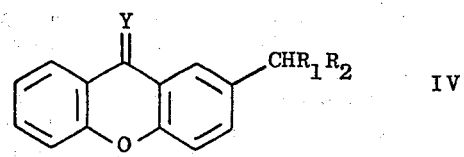

IV or the corresponding compound substituted by $R_3$ in the 1-, 3-, 4-, 5-, 6-, 7- or 8-position, wherein Y is (H,OH) or =O, and $R_1$, $R_2$ and $R_3$ have the values given in Formula I, is treated with a reducing agent; or D. a compound of general Formula V

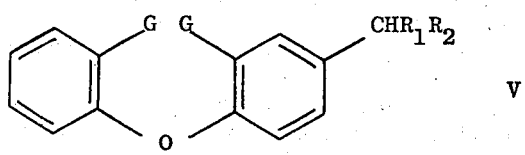

V or the corresponding compound in which one of the two benzene rings is substituted by $R_3$ at a position other than that bearing the $-CHR_1R_2$ group, and one of the two G groups is the group $CH_2X_1$, and the other group is H, in which $X_1$ is Hal or an optionally reactively functionalized hydroxy or amino group, and Hal is Cl, Br or I, and $R_1$, $R_2$ and $R_3$ have the values given in Formla I, is cyclized; and optionally thereafter a thus-obtained compound of Formula I wherein $CHR_1R_2$ is $CH_2OAc$ is solvolyzed or wherein $CHR_1R_2$ is a $CH_2OH$ is esterified.

Advantageously, the xanthene derivatives of Formula I are prepared by:

a. reacting, under conditions splitting off $HX_1$ or $MX_1$, respectively.
   i. a compound of the Formula IIaa (II, X = H or M) wherein M is MgHal or an equivalent of a metal atom or an organo-metallic group, with a compound of the formula $X_1$-$CHR_1R_2$ (VIa), or with a des-$HX_1$ derivative of such a compound, or
   ii. a compound of the Formula IIab (II, X = $X_1$) with a compound of the formula M-$CHR_1R_2$ (VIb), or
   iii. a compound of Formula IIac (II, X = $-CHR_1M$) with a compound of the formula $X_1R_2$ (VIc) or with a des-$HX_1$ derivative of such a compound, or
   iv. a compound of the Formula IIad (II, X = $-CHR_1X_1$) or a des-$HX_1$ derivative of such a compound with a compound of the formula M-$R_2$ (VId); or b. treating a compound of Formula IIb (II, X = $X_2$) wherein $X_2$ is a group oxidizable to the group $-CHR_1R_2$ and especially a group otherwise corresponding to $-CHR_1R_2$ but containing, in place of $R_1$, a group oxidizable to $R_1$, with a dehydrogenating or oxidizing agent, respectively; or c. treating a compound of Formula IIc (II, X = $X_3$) wherein $X_3$ is a group reducible to the group $-CHR_1R_2$ and corresponds especially to the group $-CHR_1R_2$ but contains, in place of $R_1$, a group reducible to $R_1$, with a reducing agent; or d. reacting a compound of Formula IId (II, X = $-CHR_2-CH_2X_4$) wherein $X_4$ is Hal or a diazonium group, with a compound of the formula $R_4OH$ wherein $R_4$ is H or Ac, or with a metallic derivative of such a compound; or e. treating a compound of Formula IIe (II, X = —CHR$_2$—X$_5$) wherein X$_5$ represents a group which can be converted into the residue R$_1$ by solvolysis, with a solvolyzing agent.

The aforementioned Formulae IIaa – IIad, as well as IIb – IIe, correspond all to Formula II wherein X in each case has the meanings indicated in the individual formulae.

In the above compounds, M can be, in addition to MgCl, MgBr or MgI, preferably an equivalent of an alkali metal atom, e.g., Li, Na, K, of an alkaline earth metal atom, e.g., Mg, Ca, or of a Cu, Cd or Zn atom, or of an organometallic group, e.g., Mg-Z, Cd-Z or Zn-Z. The term "organometallic residue" includes organoboron residues, e.g., 9-borabicyclo[3,3,1]nonyl-(9). In the X$_1$ groups, the optionally reactively functionalized hydroxy or amino groups means especially those groups which can be split off as HX$_1$ under the reaction conditions, analogously to Cl, Br or I, for example NH$_2$, NHA (wherein A is alkyl of 1–8, preferably 1–4 carbon atoms), NHAr (wherein Ar is aryl of 6–10 carbon atoms, for example phenyl, 1- or 2-naphthyl), OH, ASO$_2$O— (e.g., methanesulfonyloxy), ArSO$_2$O— (e.g., benzenesulfonyloxy, p-toluenesulfonyloxy, 1- or 2-naphthalenesulfonyloxy), AcO (e.g., acetoxy), or an etherified OH-group of preferably 1–7 carbon atoms (e.g., methoxy, benzyloxy).

The individual variants of the process are explained hereinbelow.

a. compounds (I) can be obtained, for example, by reacting xanthenes (II, X = H) with compounds (VIa) wherein X$_1$ represents preferably Cl or Br, under the conditions of a Friedel-Crafts alkylation. Especially suitable as starting compounds are, on the one hand, xanthene, haloxanthenes, such as 1-, 2-, 3- or 4-fluoroxanthene, 1-, 2-, 3- or 4-chloroxanthene, 1-, 2-, 3- or 4-bromoxanthene, and, on the other hand, 2-haloalcohols of the formula R$_2$—CHHal—CH$_2$OH, e.g., 2-chloro- or 2-bromopropanol, and/or the esters thereof. Also suitable are the des-HX$_1$ derivatives of the compounds (VIa), e.g., the corresponding unsaturated compounds, e.g., allyl alcohol and/or the esters and ethers thereof or the alkylene epoxides, e.g., propylene oxide. The reaction takes place generally according to methods described in the literature. Suitable catalysts are, for example, Lewis acids, e.g., AlCl$_3$, AlBr$_3$, BF$_3$ and the etherate thereof, BCl$_3$, BBr$_3$, ZnCl$_2$, ZnBr$_2$, FeCl$_3$, SbCl$_5$, or mineral acids, e.g., HF, H$_2$SO$_4$, H$_3$PO$_4$, or the anhdyrides thereof, e.g., P$_2$O$_5$. An inert solvent is preferably employed, e.g., hexane, 1,2-dichloroethane, 1,1,2-trichloroethane, trichloroethylene, CS$_2$, or nitrobenzene. Normally, the reaction mixture is first cooled and then the reaction is terminated at temperatures of between about 0° and 100°, preferably at room temperature. Reaction times of between about 1 and 100 hours are usually employed.

A variant of this method resides in that the compound II (X = H) is heated with a haloalcohol in the presence of a heavy metal oxide, such as Fe$_2$O$_3$ and a metal halide, e.g., KBr, to a temperature of about 100°–250°.

Compounds of Formula I are also obtainable by reacting organometallic compounds of Formulae IIaa (X = M), VIb, IIac, VId and IIae, respectively, with haloen compounds or the analogs thereof, of Formulae VIa, IIab, VIc, IIad and/or VIe, or the des-HX$_1$ derivatives, especially the dehydrohalogen derivatives of these compounds, under conditions where MX$_1$ is split off and which correspond to the conditions known for organometallic syntheses from the literature.

Typical starting compounds for this reaction are, for example, the following:

| | |
|---|---|
| Z-M (IIaa, X = M): | 2-xanthenyllithium, 2-xanthenylmagnesium chloride, bromide or iodide, bis(2-xanthenyl)-cadmium; |
| Z-X$_1$ (IIab): | 2-chloro-, 2-bromo- or 2-hydroxyxanthene; |
| Z-CHR$_1$M (IIac): | the derivatives of esters of 2-(2-xanthenyl)-ethanol, metallized in the α-position, for example by Na or an MgX$_1$ group; |
| Z-CHR$_1$X$_1$ (IIad): | the derivatives of esters of 2-(2-xanthenyl)-ethanol halogenated in the α-position; |
| X$_1$-CHR$_1$R$_2$ (VIa): | 2-haloalkanols and the esters thereof, e.g., 2-chloroethanol, 2-bromoethanol, 2-chloropropanol, furthermore the des-HX$_1$ derivatives of these compounds, e.g., ethylene oxide, propylene oxide, allyl alcohol; |
| M-CHR$_1$R$_2$ (VIb): | the Grignard compounds and organolithium compounds derived from 2-haloalcohols; |
| X$_1$R$_2$ (VIc): | alkyl halides, e.g., methyl chloride, bromide, or iodide, ethyl chloride, bromide, or iodide, n-propyl chloride, bromide, or iodide, n-butyl chloride, bromide, or iodide, and also the corresponding alcohols and the reactive esters thereof, e.g., the sulfuric acid and sulfonic acid esters, e.g., the p-toluene-sulfonates, e.g., dimethyl sulfate or ethyl p-toluenesulfonate; |
| MR$_2$ (VId): | the Grignard and organolithium compounds derived from the aforementioned halides VIc, e.g., methyllithium, methylmagnesium chloride, bromide or iodide, butyllithium. |

These starting compounds are, in part, known, or they can be prepared in a conventional manner. Thus, the halogen compounds are obtained, for example, by the direct halogenation of the halogen-free basic substances, or by reacting the corresponding hydroxy compounds with SOCl$_2$, HBr or PBr$_3$; the iodine compounds can also be prepared, for example, from the corresponding bromine compounds with KI. The organometallic compounds can be obtained, for example, by the metallization of the corresponding hydrogen or halogen compounds, e.g., with metallic Na, Li or Mg, NaH, NaNH$_2$, alkyl— or aryl-Li compounds, e.g., butyllithium or phenyllithium.

Suitable solvents for these reactions are, for example, ethers, e.g., diethyl ether, diisopropyl ether, 1,2-dimethoxyethane, tetrahdrofuran (THF), dioxane, or mixtures thereof with one another or with hydrocarbons, e.g., hexane, benzene, toluene or xylene; also amides, e.g., dimethylformamide (DMF), hexamethylphosphoric triamide and sulfoxides, e.g., dimethyl sulfoxide (DMSO). The reaction temperatures range normally from about −20° to 180°, preferably from 0° to 70°; the reaction times generally are from 0.5 to 72 hours.

It is also possible to employ an organometallic compound of especially Formula IIaa, but also of Formulae VIb, IIac or VId, respectively, wherein M is an organoboron group, particularly a 9-borabicyclo[3,3,1]nonyl-(9) group. These starting compounds are obtainable, for example, by reacting the corresponding organolithium compounds with 9-borabicyclo[3,3,1]-nonane in ether at a temperature of from about −10° to +20°, and subsequent acidification. They are normally not isolated. The actual reaction of these organoboron compounds with the compounds of Formula VIa, but also IIab, VIc and IIad, respectively, is suitably accomplished with the addition of a lower tertiary alkanol and an excess of a lower alkali metal tert.-alkoxide, preferably K-tert.-butylate or -pentylate, at a temperature of from about −10° to +20°.

b. For the preparation of the compounds of Formula I, it is further possible to treat compounds of the formula Z-X$_2$ (IIb) with a dehydrogenating and/or oxidizing agent.

Suitable starting compounds of Formula IIb are, for example, compounds of the formula Z–CHR$_2$–CH$_2$R$_5$ (wherein R$_5$ is a borane, boroalkyl or aluminumalkyl group, an alkali metal or an alkaline earth metal halide group).

These compounds need not be isolated in the pure form. Rather, they can be oxidized directly in the reaction mixture wherein they were formed. For example, an ethylene derivative of the formula Z—CR$_2$=CH$_2$ is first reacted with diborane. Then, for example, a B$_2$H$_6$ solution or a complex borohydride, e.g., NaBH$_4$, and a Lewis acid, e.g., BF$_3$ etherate, are added to a solution of the olefin in, e.g., THF or di- or triethylene glycol dimethyl ether at a temperature from about −80° to the boiling point of the solvent, and the thus-formed trisubstituted borane is oxidized, for example with H$_2$O$_2$, optionally after decomposing the excess complex hydride with water, with the addition of a base, e.g., NaOH, preferably at a temperature from 20° to 60°. In place of diborane, it is also possible to use alkylaluminum compounds which can be added analogously and can be split by oxidation.

Furthermore, in order to convert the xanthenyl ethyl metal and/or metal halide compounds of the formula Z—CHR$_2$—CH$_2$—M, obtainable by the reaction of halides of the formula Z—CHR$_2$—CH$_2$—Hal with alkali metals, preferably Li, or alkaline earth metals, preferably Mg, into compounds of Formula I wherein R$_1$ is CH$_2$OH, these compounds can be treated with an oxidizing agent. In a preferred mode of operation for this method, oxygen is passed through a solution of the corresponding Grignard compound of the formula Z—CHR$_2$—CH$_2$MgHal in an inert solvent, e.g., ether, THF or dioxane at a temperature of about 40° to 100°. After the usual working-up operation, alcohols of the formula Z—CHR$_2$CH$_2$OH are obtained.

c. Compounds of Formula I are furthermore obtainable by the reduction of compounds of Formula IIc.

Typical compounds of Formula IIc are, for example, those of Formulae IIca, IIcb, IIcc or IIcd:

   IIca wherein R$_6$ is an alkylidene residue of up to 4 carbon atoms, corresponding to R$_2$;

   IIcb wherein R$_7$ is (H,CHO), =CHOAc, (H,CN), (H,CH$_2$OR$_8$), (H,COHal), (H,CON$_3$), (H,CONH$_2$), (H,CO—O—CO—OA), or —O—CH$_2$—, and R$_8$ is a group which can be split off by hydrogenolysis, e.g., benzyl, diphenylmethyl, triphenylmethyl or carbobenzoxy;

   IIcc wherein R$_9$ is a group removable by hydrogenolysis, especially OH, OAc, Hal, SH, NH$_2$, aralkyloxy or aralkylamino of respectively up to 10 carbon atoms;

   IIcd wherein R$_{10}$ is a free or functionally modified, especially esterified COOH-group.

The reduction of these starting compounds can be effected advantageously by catalytic hydrogenation or by chemical methods. The starting compound can be treated, for example, in the presence of a catalyst with hydrogen under a pressure of from 1 to about 200 atmospheres and at a temperature of from about −80° to 200°, preferably from 20° to 100°. Suitably, the hydrogenation is carried out in the presence of an inert solvent, e.g., water, aqueous sodium hydroxide solution, a lower alcohol, e.g., methanol, ethanol, isopropanol, n-butanol, an ester, e.g., ethyl acetate, an ether, e.g., THF or dioxane, a carboxylic acid, e.g., acetic acid or propionic acid. It is also possible to utilize solvent mixtures. For purpose of hydrogenation, the free compound IIc or the corresponding salt, e.g., the sodium salt, can be employed. Advantageous catalysts are, for example, noble metal, nickel, and cobalt catalysts. The noble metal catalysts can be provided on supports (e.g., on charcoal, calcium carbonate or strontium carbonate), as oxide catalysts, or as finely divided metal catalysts, preferably, platinum and palladium, or for example, ruthenium or rhodium. Nickel and cobalt catalysts are advantageously used as the Raney metals, and nickel is also employed on kieselguhr or pumice as the support. Also usable as the catalyst is copper chromium oxide.

Another reducing method for the compounds IIc is the reaction with nascent hydrogen. This hydrogen can be produced, for example, by treating metals with acids or bases. Thus, it is possible, for instance, to use systems such as zinc/acid, zinc/alkaline solution, iron/acid and tin/acid. Suitable acids are, for example, hydrochloric acid and acetic acid. Also sodium or another alkali metal in a lower alcohol, such as ethanol, isopropanol, n-butanol, amyl alcohol, isoamyl alcohol or also phenol, is suitable for producing the nascent hydrogen. Also suitable for this purpose is an aluminum-nickel alloy in an alkaline-aqueous solution, optionally with the addition of methanol, as well as sodium or aluminum amalgam in an aqueous-alcoholic or aqueous solution. In this reducing method, temperatures are used of about 0° to about 150°, preferably from 20° to the boiling point of the solvent employed.

Furthermore, suitable reducing agents are metal hydrides, especially complex metal hydrides. This is advantageous, in particular, if the starting compounds are acids of the formula Z—CHR$_2$—COOH or the esters thereof. Suitable hydrides of this type are, e.g., lithium aluminum hydride, also sodium borohydride, for example, in the presence of aluminum chloride or lithium bormide, and further, calcium borohydride, magnesium borohydride, sodium aluminum hydride, lithium and sodium alkoxyaluminum hydrides, sodium trialkoxy-borohydrides, e.g., sodium trimethoxyborohydride. Also suitable as reducing agents are dialkyl aluminum hydrides, e.g., diisobutyl aluminum hydride. These reducing reactions are advantageously conducted in the presence of an inert solvent, e.g., an ether, such as, for example, diethyl ether, THF, dioxane, 1,2-dimethoxyethane, or diglyme. Sodium borohydride can also be used in an aqueous or aqueous-alcoholic solution. The reaction is advantageously accomplished at temperatures of between −80° and +100°, especially between 20° and the boiling point of the solvent used, wherein an inert gas, e.g., N$_2$ or argon, can be used as the reaction atmosphere.

An additional reducing agent which is particularly suitable for the removal of a tertiary OH-group in a starting compound of the formula $Z—CR_1R_2—OH$, is tin(II) chloride, which is utilized especially in the form of a dihydrate in an aqueous, aqueous-alcoholic, or aqueous-acidic solution, for example, in the presence of acetic acid and/or hydrochloric acid, suitably at a temperature of about 0° to 120°.

Further advantageous reducing agents include hydrogen iodide, sodium dithionite in an alkaline or ammoniacal solution; iron(II) hydroxide; hydrogen sulfide and the derivatives thereof, especially metal hydrogen sulfides, metal sulfides and polysulfides; $SO_2$ and its derivatives, e.g., bisulfites and sulfites.

It is also possible to reduce, in compounds of Formula IIc, one or more carbonyl groups to $CH_2$-groups according to the methods known from the literature as devised by Clemmensen (e.g., with zinc and hydrochloric acid at temperatures of between 20° and 130°) or Wolff-Kishner (e.g., with hydrazine at reaction temperatures of between 100° and 250° or with hydrazine hydrate in a high-boiling water-miscible solvent, e.g., diethylene glycol or triethylene glycol, and/or in the presence of a strong base, e.g., NaOH, KOH, or K-tert.-butylate).

It is also possible to replace Hal atoms by hydrogen, which is done by converting the corresponding Hal compounds into the associated organometal compounds, e.g., Grignard compounds, which are then hydrolyzed with water or dilute acid.

With the aid of the above-described methods, it is possible to reduce several reducible groups in a given starting substance, wherein the compounds of Formula IIc are obtained as intermediate stages in the reaction, but need not be isolated. Furthermore, a group $R_1$ present in the starting substance can be reduced to another group $R_1$.

d. Compounds of Formula I are also obtained by subjecting a halogen compound of the formula $Z—CHR_2—CH_2Hal$ (IId, $X_4$ = Hal) to hydrolysis or acidolysis, or by reacting this compound with a metallic salt of a fatty acid of the formula AcOH (e.g., sodium acetate).

Thus, alcohols of Formula I ($R_1 = CH_2OH$) are obtained, for example, by saponifying the halogen compound in an aqueous or aqueous-alcoholic solution or suspension, optionally with the addition of a solubilizer, e.g., an alcohol, glycol or polyglycol ether. Preferred saponifying agents are alkali, e.g., NaOH or KOH and also slurries of $Ca(OH)_2$, $Pb(OH)_2$ or AgOH. The saponification is effected ordinarily at an elevated temperature, e.g., at the boiling temperature of the solvent. The halogenide can, however, also be reacted in an anhydrous medium, by agitating the solution of the halogenide in an inert solvent, e.g., in acetone, ether, THF, acetonitrile or benzene under boiling temperatures with suspended AgOH or $Pb(OH)_2$.

Esters of Formula I ($R_1 = CH_2OAc$) are obtained by refluxing compounds of Formula IId in an aqueous, aqueous-alcoholic, or alcoholic solution with an alkali metal salt of the carboxylic acid to be esterified.

If it is desired to produce acetates of the formula $Z—CHR_2—CH_2OCOCH_3$, a halogenide of the formula $Z—CHR_2—CH_2Hal$ can be refluxed with anhydrous sodium acetate in acetic acid. It is also possible to reflux a halogen compound of the formula $Z—CHR_2—CH_2Hal$ in an inert solvent, e.g., ether, acetone, chloroform, THF or benzene, with a suspension of the silver or lead salt of the acid to be esterified.

Diazonium compounds of Formula IId ($X_4$ = a diazonium group) are produced during the treatment of amines of the formula $Z—CHR_2—CH_2NH_2$ with nitrous acid or the derivatives thereof, for example alkyl nitrites or NOCl. These compounds are split in the presence of water to alcohols of Formula I ($R_1 = CH_2OH$), according to methods known from the literature. In this case, the reaction is especially advantageously accomplished by combining an aqueous solution of $NaNO_2$ with a mineral acid or acetic acid solution of the amine at a temperature of 0°–100° and terminating the reaction by heating. If the reaction is effected in the presence of an acid, e.g., acetic acid, the thus-obtained reaction product is also an ester of Formula I ($R_1 = CH_2OAc$).

e. Compounds of Formula I are also obtained by solvolysis, preferably hydrolysis, of compounds of Formula IIe in accordance with methods described in the literature. The compounds IIe are preferably esters wherein $X_5$ is an esterified $CH_2OH$-group different from $CH_2OAc$.

The solvolysis, especially hydrolysis, can be accomplished in an acidic, neutral, or alkaline medium at a temperature from about −20° to about 200°, preferably from room temperature to the boiling temperature of the selected solvent. Suitable acidic catalysts are, for example, hydrochloric acid, sulfuric acid, phosphoric acid, and hydrobromic acid, and suitable basic catalysts are, e.g., sodium hydroxide, potassium hydroxide, calcium hydroxide, sodium carbonate and potassium carbonate.

As the solvent, water is preferred. Other suitable solvents are lower alcohols, ether, e.g., THF and dioxane; amides, e.g., DMF; sulfones, e.g., tetramethylenesulfone; acetic acid; or mixtures thereof, expecially aqueous mixtures.

It is also possible to convert ethers of Formula IIe wherein $X_5$ is an etherified $CH_2OH$-group, into compounds of Formula I by a solvolytic splitting reaction, for example, by treatment with HBr or HI in an aqueous or acetic solution, by heating with a Lewis acid, e.g., $AlCl_3$, or a boron trihalide, or by melting with a pyridine hydrohalide or aniline hydrohalide at about 200°.

Esters of Formula I ($R_1 = CH_2OAc$) can be obtained by solvolysis. In this reaction, compounds of Formula IIe wherein $X_5$ is a thioester, iminoether, oximinoether, hydrazone ether, thioamide, amidine, amidoxime, or amide hydrazone group, are solvolyzed with water or dilute aqueous bases or acids, e.g., ammonia, NaOH, KOH, $Na_2CO_3$, $K_2CO_3$, HCl, $H_2SO_4$, with the addition of the respective alcohol and splitting off of hydrogen sulfide, ammonia, amines, hydrazine derivatives, or hydroxylamine, suitably at a temperature of 20° to 100°.

The compounds (I) are also obtainable by splitting off a fragment of the formula $E_1$–$E_2$ from a compound of Formula III. One of the two groups E in III is a phenolic hydroxy group, which can also be present in the form of a metallic salt (phenolate) derived therefrom, preferably in the form of a sodium salt. The other of the two E groups can be the same or it can also be a halogen atom, preferably Cl or Br, a nitro group or amino group, or a functionalized, e.g., etherified or esterified, OH— or SH—group. The compound $E_1$—$E_2$ to be split off can accordingly represent, for example, water, HNO$_2$, ammonia, hydrogen halide, such as HCl or HBr, hydrogen sulfide. Depending on the constitution of the starting compounds, the agents used to split off E$_1$—E$_2$ are dehydrating agents and/or acids, e.g., ZnCl$_2$, P$_2$O$_5$, polyphosphoric acid, or bases, e.g., NaOH, KOH, Ca(OH)$_2$, or K$_2$CO$_3$, optionally in the presence of a catalyst, e.g., a heavy metal, for example, copper, preferably in pulverized form. The splitting-off step can be effected in the presence of an additional inert, preferably high-boiling solvent, e.g., in the presence of xylene or tetrahydronaphthalene ("Tetralin"). However, the reaction is preferably conducted in the absence of a solvent. The reaction temperatures range from about 0° to about 250°, preferably from 80° to 220°.

It is also possible to conduct the reaction so that the starting material (III) is not isolated but rather is produced in situ in the reaction mixture. Thus, it is possible to start with a compound which otherwise corresponds to Formula III, but wherein both E groups are amino groups, which are subsequently diazotized and concentrated by boiling. As the intermediate product which is not isolated, a diphenol (III, both E groups = OH) is formed which is dehydrated by heating in an acidic solution. Furthermore, it is possible, for example, to heat a salicyl alcohol optionally substituted by the group R$_3$ together with a p-hydroxyphenyl alkanol, wherein the thus-produced intermediate product is probably the aforementioned diphenol or a compound V (one of the groups G = CH$_2$OH; see below).

The xanthenes of Formula I are obtainable by the reduction of the corresponding 9-hydroxyxanthene derivatives [IV, Y = (H,OH)] or xanthones (IV, Y = O). This can be accomplished advantageously in accordance with one of the above-described methods, preferably by catalytic hydrogenation or in accordance with the Clemmensen or Wolff-Kishner methods.

Furthermore, the compounds (I) are obtainable by cyclizing a compound (V), thus splitting off HX$_1$. For example, it is possible to dehydrate an o-hydroxymethyldiphenyl ether of Formula V (one group G = CH$_2$OH) to a xanthene derivative of Formula I by heating for one-half to several hours at 150°–200° in the presence of a metallic oxide, e.g., Cu$_2$O, ZnO or MgO. A hydroxy compound (V, one group G = CH$_2$OH) can also be produced as an intermediate product during the reaction of a salicyl alcohol, optionally substituted by the group R$_3$, with a p-hydroxyphenyl alkanol.

Optionally, in a thus-obtained product of Formula I, a —CH$_2$OAc group can be solvolyzed, especially hydrolyzed, to the —CH$_2$OH group in accordance with methods described in the literature. The solvolysis, especially hydrolysis (saponification) of these esters is suitably conducted under similar or the same conditions as the solvolysis of compounds IIe. Preferably, the esters are treated for about 1–48 hours with K$_2$CO$_3$ in methanol, ethanol or isopropanol at a temperature of about 20° to 80°.

Furthermore, in accordance with methods disclosed in the literature, an alcohol of Formula I (R$_1$ = CH$_2$OH) is reacted with a carboxylic acid of the formula AcOH, preferably in the presence of an inorganic or organic acid, e.g., HCl, HBr, HI, H$_2$SO$_4$, H$_3$PO$_4$, trifluoroacetic acid, a sulfonic acid, e.g., benzenesulfonic acid or p-toluenesulfonic acid, or an acidic ion exchanger, as well as optionally in the presence of an inert solvent, such as, for example, benzene, toluene or xylene, at a temperature of about 0° to preferably the boiling temperature.

During the esterification, the water of reaction can be removed azeotropically. Advantageously, a hydrocarbon, e.g., benzene or toluene, or a chlorinated hydrocarbon, e.g., chloroform or 1,2-dichloroethane, is added to the reaction mixture for this purpose. Under gentle conditions, the esterification can be accomplished by binding the water of reaction chemically by the addition of a carbodiimide, e.g., N,N'-dicyclohexylcarbodiimide. Inert solvents, e.g., ether, dioxane, 1,2-dimethoxyethane, benzene, CH$_2$Cl$_2$ or CHCl$_3$, are employed and a base, e.g., pyridine, can be added.

Alcohols of the Formula I (R$_1$ = CH$_2$OH) or the alkali metal alcoholates thereof can also be reacted with the halogenides or anhydrides of the acids to be esterified, with or without the addition of an acid-neutralizing agent, e.g., sodium or potassium hydroxide, sodium or potassium carbonate, or pyridine. Suitable solvents are inert organic solvents, e.g., ether, THF, and benzene. It is also possible to utilize the excess halogenides or anhydrides as the solvent. In a preferred mode of operation, the alcohol of Formula I (R$_1$ = CH$_2$OH) is combined in a pyridine solution with the halogenide or anhydride of the acid to be esterified.

It is also possible to esterify alcohols of Formula I (R$_1$ = CH$_2$OH) with ketenes, preferably in an inert solvent, e.g., ether, benzene or toluene, and with the addition of an acidic catalyst, such as, for example, sulfuric acid or p-toluenesulfonic acid.

The esters of Formula I (R$_1$ = CH$_2$OAc) can also be obtained by the transesterification of alcohols of Formula I (R$_1$ = CH$_2$OH) with an excess of a lower alkyl ester, e.g., of the formula AcOA. The reaction is carried out in accordance with the transesterification method described in the literature, especially in the presence of basic or acidic catalysts, e.g., sodium ethylate or sulfuric acid, at a temperature of about 0° to the boiling point of the reaction mixture. Preferably, after the equilibrium has been attained, one of the reactants is withdrawn from this equilibrium by distillation.

In case the compounds of Formula I contain a center of asymmetry, they are ordinarily present in the racemic form.

The racemates can be separated into their optical antipodes according to methods known from the literature. Chemical separation is preferred. According to this method, diastereomers are formed from the racemic mixture by reaction with an optically active auxiliary agent. Thus, ester diastereomers can be produced by the esterification of compounds of Formula I (R$_1$ = CH$_2$OH) with optically active acids. The thus-obtained mixtures of diastereomeric esters can be separated by selective crystallization. By hydrolytic separation of the isolated diastereomeric compound, the desired optically active compounds of Formula I are produced. Furthermore, it is of course also possible to obtain optically active compounds in accordance with the above-described methods, by the use of starting substances which are already optically active.

The compounds of Formula I an be utilized as drugs in human or veterinary medicine, ordinarily in a mixture with a solid, liquid, and/or semiliquid excipient, i.e., pharmaceutically acceptable vehicle. Suitable vehicles are those organic or inorganic materials suitable for parenteral, enteral or topical application and which do not react with the active compound in admixture therewith, such as, for example, water, vegetable oils, benzyl alcohols, polyethylene glycols, gelatin, lactose, amylose, magnesium stearate, talc, vaseline, cholesterol. Especially suitable for parenteral administration are solutions, preferably oily or aqueous solutions, as well as suspensions, emulsions or implants. Suitable for enteral application are tablets, dragees, capsules, syrups, elixirs or suppositories, and for topical application, ointments, creams or powders. The abovedisclosed preparations can optionally be sterilized or they can contain auxiliary substances, such as lubricants, preservatives, stabilizers or wetting agents, emulsifiers, salts to influence the osmotic pressure, buffer substances, coloring, flavoring and/or aromatic substances.

The compounds are preferably administered in dosages of between 1 and 500 mg. per dosage unit. The preferred normal dosage range is between 0.1 and 30 mg/kg. The compounds are preferably applied enterally, particularly orally.

The temperatures herein are set forth in degrees Celsius. "Work up as usual" means the following: If necessary, water is added, the reaction mixture is extracted with ethyl acetate, ether, or chloroform, then separated, and the organic extract is washed with water, dried over sodium sulfate, filtered, the solvent distilled off, and the residue distilled and/or crystallized from the solvent indicated in parentheses. DMF = dimethylformamide, DMSO = dimethyl sulfoxide, THF = tetrahydrofuran.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

EXAMPLE 1

A mixture of 11 g. of xanthene, 1.3 g. of 2-chloropropanol, 0.015 g. of $Fe_2O_3$, and 0.007 g. of KBr is heated for 15 hours to 200°. The reaction product is taken up in ether. After working the mixture up as usual, 2-(2-xanthenyl)-propanol is obtained, m.p. 86°–89° (diisopropyl ether).

EXAMPLE 2

14 g. of pulverized anhydrous $AlCl_3$ is added to a solution of 18.2 g. of xanthene in 200 ml. of nitrobenzene; at 20°–25°, 10 g. of 2-chloropropanol is then added dropwise to the reaction mixture. The latter is agitated overnight at 20°, then heated for 3 hours on a steam bath, decomposed by adding ice, and the nitrobenzene is driven off with steam. After working up the mixture as usual, 2-(2-xanthenyl)-propanol is produed, m.p. 86°–89°.

In place of $AlCl_3$, it is also possible to employ equivalent amounts of $AlBr_3$, $BF_3$ or the etherate thereof, $BCl_3$, $BBr_3$, $ZnCl_2$, or $ZnBr_2$, and in place of the 2-chloropropanol, equivalent quantities of 2-bromo- or 2-iodopropanol can be used.

EXAMPLE 3

14 g. of pulverized anhydrous $AlCl_3$ is added to a solution of 18.2 g. of xanthene in 150 ml. of trichloroethylene; at 0°–5°, a solution of 8 g. of ethylene oxide in 50 ml. of trichloroethylene is added dropwise to the reaction mixture. The latter is stirred for 12 hours at 5°–10°, decomposed by adding ice, worked up as usual, and the product is 2-(2-xanthenyl)-ethanol.

Analogously, 2-(2-xanthenyl)-propanol is obtained with propylene oxide.

EXAMPLE 4

14 g. of pulverized anhydrous $AlCl_3$ is added to a solution of 18.2 g. of xanthene in 200 ml. of trichloroethylene; under cooling to below +5°, 7 g. of allyl alcohol in 20 ml. of trichloroethylene is added dropwise to the reaction mixture. The latter is allowed to reach room temperature, agitated for 12 hours, decomposed by adding ice, worked up as usual, and the thus-obtained product is 2-(2-xanthenyl)-propanol, m.p. 86°–89°.

With 2-buten-1-ol, 2-(2-xanthenyl)-1-butanol is produced.

EXAMPLE 5

A solution of 13.9 g. of 2-bromopropanol in 20 ml. of THF is added at 20° to a bis(2-xanthenyl)-cadmium solution (obtained by adding dropwise 26.1 g. of 2-bromoxanthene in 300 ml. of THF to 2.5 g. of Mg filings in 100 ml. of THF under agitation and reflux, adding thereto 20 g. of cadmium chloride, and boiling for 10 minutes); this mixture is allowed to stand for 24 hours at 20°. After working the mixture up as usual, 2-(2-xanthenyl)-propanol is obtained, m.p. 86°–89°.

EXAMPLE 6

A solution of 2-xanthenyllithium (obtained from 26.1 g. of 2-bromoxanthene and 1.4 g. of lithium in 300 ml. of ether) is added to a solution of 12.2 g. of 9-borabicyclo[3,3,1]nonane in 100 ml. of THF at 0°. The mixture is agitated at 0° for 1 hour, 9.5 g. of methanesulfonic acid is added thereto, and the mixture is stirred for another hour. Then, a solution of 13.9 g. of 2-bromopropanol in 50 ml. of ether and thereafter a suspension of 25 g. of potassium tert.-butylate in 100 ml. of tert.-butanol are added to the reaction mixture. The latter is maintained at 10° for 24 hours, acidified with 500 ml. of 6N hydrochlorid acid, refluxed for 6 hours, cooled, worked up as usual, and the product is 2-(2-xanthenyl)-propanol, m.p. 86°–89°.

EXAMPLE 7

2.61 g. of 2-bromoxanthene is reacted with 0.5 g. of magnesium filings in 60 ml. of absolute THF while adding a trace of iodine and while heating the reaction mixture. In incremental portions, 10 g. of 2-iodopropanol is added thereto and the mixture refluxed for 20 hours under agitation. Thereafter, the mixture is evaporated to dryness, worked up as usual, and the product is 2-(2-xanthenyl)-propanol, m.p. 86°–89°.

EXAMPLE 8

Under agitation and cooling, a solution of 5.8 g. of propylene oxide in 10 ml. of absolute ether is added at 0°–5° to a solution obtained from 2.6 g. of Mg filings and 26.1 g. of 2-bromoxanthene in 120 ml. of absolute ether; the mixture is allowed to stand overnight. Thereafter, 80 ml. of benzene is added thereto, the ether is distilled off, and the benzenic solution is refluxed for 1 hour. After decomposition with aqueous $NH_4Cl$ solution and after working up the mixture as usual, 2-(2-xanthenyl)-propanol is obtained, m.p. 86°–89°.

EXAMPLE 9

22.2 g. of 2-(2-propenyl)-xanthene is dissolved in 50 ml. of diglyme and mixed with 30 ml. of a 1-molar solution of $NaBH_4$ in diglyme. Under agitation and introduction of $N_2$, a solution of 5.6 g. of freshly distilled BF$_3$ etherate in 12 ml. of diglyme is added gradually dropwise within 30 minutes to this solution. The reaction mixture is combined with 7 ml. of water. Then, 14 ml. of a 3N NaOH solution and 14 ml. of 30% H$_2$O$_2$ are added dropwise at 80°–100°. The reaction mixture is cooled, mixed with ice water, worked up as usual, and the product is 2-(2-xanthenyl)-propanol, m.p. 86°–89°.

EXAMPLE 10

3.03 g. of 2-(1-bromo-2-propyl)-xanthene is reacted with 0.26 g. of Mg filings in 100 ml. of ether. The mixture is cooled to −5°, oxygen is introduced for 4 hours, and the mixture is combined with aqueous NH$_4$Cl solution. The usual working-up step yields 2-(2-xanthenyl)-propanol, m.p. 86°–89°.

EXAMPLE 11

One gram of crude 2-(2-xanthenyl)-2-propenol [obtainable by reducing the ethyl ester of 2-(2-xanthenyl)-acrylic acid with LiAlH$_4$] is dissolved in 25 ml. of dioxane, mixed with 0.1 g. of PtO$_2$, and hydrogenated at 20° and under normal pressure until the hydrogen absorption is terminated. The product is filtered, concentrated by evaporation, and 2-(2-xanthenyl)-propanol is thus obtained, m.p. 86°–89°.

In place of the dioxane, it is also possible to use ethyl acetate, and in place of PtO$_2$, 5% Pd/C can also be utilized.

EXAMPLE 12

23.8 g. of 2-(2-xanthenyl)-2-propenol is refluxed for 3 hours in 140 ml. of 1N sodium hydroxide solution and 300 ml. of ethanol. 400 ml. of water is added to the reaction mixture and at 25° 550 g. of 2.5% sodium amalgam is introduced in incremental portions under agitation during the course of 5 hours; the mixture is vigorously agitated for another 5 hours, heated on a water bath, decanted off from the mercury, the alcohol is distilled off, and the mixture is worked up as usual, thus obtaining 2-(2-xanthenyl)-propanol, m.p. 86°–89°.

EXAMPLE 13

A solution of 31 g. of the ethyl ester of 2-(2-xanthenyl)-propionic acid (m.p. 54°–57°; obtainable by reacting xanthene with ethoxalyl chloride in 1,2-dichloroethane in the presence of AlCl$_3$ at 5°–10°, reacting the thus-produced ethyl ester of 2-xanthenyl-glyoxylic acid [b.p. 192°–197°/0.1 mm.] with CH$_3$MgI in ether, and reducing the resultant oily ethyl ester of 2-(2-xanthenyl)-2-hydroxypropionic acid with SnCl$_2$ in HCl/ethanol) in 250 ml. of absolute THF is added dropwise to a suspension of 4.2 g. of LiAlH$_4$ in 250 ml. of absolute THF. The mixture is refluxed for 30 minutes, cooled, and under ice cooling a mixture of 20 ml. of THF, 5 ml. of water, and 15 ml. of 32% sodium hydroxide solution is added dropwise thereto. The mixture is filtered over kieselguhr, dried, evaporated, and the product is 2-(2-xanthenyl)-propanol, m.p. 86°–89°.

Analogously, the following compounds are obtained by reducing the corresponding esters with LiAlH$_4$:

2-(2-xanthenyl)-ethanol
2-(1-fluoro-2-xanthenyl)-propanol
2-(3-fluoro-2-xanthenyl)-propanol
2-(4-fluoro-2-xanthenyl)-propanol
2-(5-fluoro-2-xanthenyl)-propanol
2-(6-fluoro-2-xanthenyl)-propanol
2-(7-fluoro-2-xanthenyl)-propanol
2-(8-fluoro-2-xanthenyl)-propanol
2-(1-chloro-2-xanthenyl)-propanol
2-(3-chloro-2-xanthenyl)-propanol
2-(4-chloro-2-xanthenyl)-propanol
2-(5-chloro-2-xanthenyl)-propanol
2-(6-chloro-2-xanthenyl)-propanol
2-(7-chloro-2-xanthenyl)-propanol
2-(8-chloro-2-xanthenyl)-propanol
2-(1-bromo-2-xanthenyl)-propanol
2-(3-bromo-2-xanthenyl)-propanol
2-(4-bromo-2-xanthenyl)-propanol
2-(5-bromo-2-xanthenyl)-propanol
2-(6-bromo-2-xanthenyl)-propanol
2-(7-bromo-2-xanthenyl)-propanol
2-(8-bromo-2-xanthenyl)-propanol
2-(2-xanthenyl)-1-butanol
2-(2-xanthenyl)-1-pentanol
2-(2-xanthenyl)-3-methyl-1-butanol
2-(2-xanthenyl)-1-hexanol
2-(2-xanthenyl)-4-methyl-1-pentanol.

EXAMPLE 14 a. 13.9 g. of the ethyl ester of 2-(2-xanthenyl)-acrylic acid is refluxed for 15 hours together with 2 g. of LiAlH$_4$ in 200 ml. of absolute THF. Thereafter, the mixture is combined with 20 ml. of 25% NaOH solution, the THF phase is decanted off, the residue is washed twice with ether, the combined organic phases are dried, and evaporated. The residue is dissolved in 200 ml. of absolute THF, 2 g. of LiAlH$_4$ is added, and the mixture is again refluxed for 8 hours. The mixture is worked up as above, thus obtaining 2-(2-xanthenyl)-propanol, m.p. 86°–89°.

Analogously, the remaining alcohols of Formula I (R$_1$ = CH$_2$OH) are obtained by reduction of the corresponding esters.

b. One gram of 2-(2-xanthenyl)-propanol is allowed to stand for 24 hours in 5 ml. of pyridine and 5 ml. of acetic anhydride. The mixture is concentrated, worked up as usual, and the product is 2-(2-xanthenyl)-propyl acetate, m.p. 62°–64°.

Analogously, the following products are obtained from the corresponding alcohols;

2-(2-xanthenyl)-ethyl acetate
2-(1-fluoro-2-xanthenyl)-propyl acetate
2-(3-fluoro-2-xanthenyl)-propyl acetate
2-(4-fluoro-2-xanthenyl)-propyl acetate
2-(5-fluoro-2-xanthenyl)-propyl acetate
2-(6-fluoro-2-xanthenyl)-propyl acetate
2-(7-fluoro-2-xanthenyl)-propyl acetate
2-(8-fluoro-2-xanthenyl)-propyl acetate
2-(1-chloro-2-xanthenyl)-propyl acetate
2-(3-chloro-2-xanthenyl)-propyl acetate
2-(4-chloro-2-xanthenyl)-propyl acetate
2-(5-chloro-2-xanthenyl)-propyl acetate
2-(6-chloro-2-xanthenyl)-propyl acetate
2-(7-chloro-2-xanthenyl)-propyl acetate
2-(8-chloro-2-xanthenyl)-propyl acetate
2-(1-bromo-2-xanthenyl)-propyl acetate
2-(3-bromo-2-xanthenyl)-propyl acetate
2-(4-bromo-2-xanthenyl)-propyl acetate
2-(5-bromo-2-xanthenyl)-propyl acetate
2-(6-bromo-2-xanthenyl)-propyl acetate
2-(7-bromo-2-xanthenyl)-propyl acetate
2-(8-bromo-2-xanthenyl)-propyl acetate
2-(2-xanthenyl)-1-butyl acetate
2-(2-xanthenyl)-1-pentyl acetate
2-(2-xanthenyl)-3-methyl-1-butyl acetate 2-(2-xanthenyl)-1-hexyl acetate
2-(2-xanthenyl)-4-methyl-1-pentyl acetate.

EXAMPLE 15

At −70°, 14.1 g. of the ethyl ester of 2-(2-xanthenyl)-propionic acid is added dropwise within 1 hour to a solution of 7.3 g. of diisobutyl aluminum hydride in 150 ml. of absolute hexane. The mixture is agitated for 1 hour at −70°, decomposed with aqueous $NH_4Cl$ solution, the hexane phase is separated, and the aqueous phase is extracted with ether. The ether/hexane solution is dried and concentrated by evaporation. The residue is chromatographed on silica gel with benzene/hexane (9 : 1), thus obtaining 2-(2-xanthenyl)-propanol.

EXAMPLE 16

13.6 g. of 2-(2-xanthenyl)-propionyl chloride is dissolved in 150 ml. of ether and gradually added dropwise to a suspension of 2 g. of $LiAlH_4$ in 100 ml. of ether. The mixture is agitated for 4 hours at 25°, decomposed with methanol, then with 15% aqueous sodium hydroxide solution, worked up as usual, and the product is 2-(2-xanthenyl)-propanol, m.p. 86°–89°.

EXAMPLE 17

2.54 g. of 2-(2-xanthenyl)-propionic acid is dissolved in 20 ml. of absolute THF and combined with 1 ml. of triethylamine. At −10°, a solution of 0.6 ml. of ethyl chloroformate in 4 ml. of THF is added dropwise within 15 minutes, the mixture is stirred for 30 minutes at −10° and then 0.5 g. of $NaBH_4$ is introduced into the solution which contains the mixed anhydride of monoethyl carbonate and the aforementioned acid, 2-(2-xanthenyl)-4,6-dioxaoctane-3,5-dione. Thereafter, the mixture is stirred for 90 minutes at 25°, 10 ml. of water is added, the mixture extracted with ether, evaporated, and the thus-obtained residue refluxed for 30 minutes with a solution of 0.25 g. of KOH in 10 ml. of ethanol. After the ethanol has been distilled off, the mixture has been worked up as usual, and the product chromatographed on $Al_2O_3$, 2-(2-xanthenyl)-propanol is obtained, m.p. 86°–89°.

EXAMPLE 18

7.6 g. of the ethyl ester of 2-chloro-2-(2-xanthenyl)-propionic acid is dissolved in 70 ml. of absolute ether and gradually added dropwise to a suspension of 2.2 g. of $LiAlH_4$ in 100 ml. of ether. The mixture is refluxed for several hours, methanol is added thereto, and the mixture is worked up as usual, thus obtaining 2-(2-xanthenyl)-propanol, m.p. 86°–89°.

EXAMPLE 19

18 ml. of a 1-molar ether $LiAlH_4$ solution is added to a suspension of 10.7 g. of anhydrous $AlCl_3$ in 50 ml. of absolute ether. Within one hour, a solution of 4.74 g. of 1-methyl-1-(2-xanthenyl)-ethylene oxide (obtainable by reacting 2-isopropenyl xanthene with N-bromosuccinimide in the aqueous phase to the corresponding bromohydrin and splitting off HBr with sodium hydroxide solution) in 70 ml. of absolute ether is added dropwise to the reaction mixture. The latter is refluxed for 2 hours, hydrolyzed by adding 10 ml. of water and 100 ml. of 10% sulfuric acid, worked up as usual, and the product is 2-(2-xanthenyl)-propanol, m.p. 86°–89°.

EXAMPLE 20

27.05 g. of 2-(2-xanthenyl)-acryloyl chloride (obtainable from the acid with $SOCl_2$ in benzene) is added dropwise under agitation at 20° to a suspension of 4 g. of $LiAlH_4$ in 300 ml. of ether. The mixture is agitated for 3 hours at 20°, methanol is added, and the mixture worked up as usual, thus obtaining 2-(2-xanthenyl)-propanol, m.p. 86°–89°.

EXAMPLE 21

25.6 g. of 2-(2-xanthenyl)-propane-1,2-diol (obtainable by reducing the ethyl ester of 2-hydroxy-2-(2-xanthenyl)-propionic acid with $LiAlH_4$) is hydrogenated in 500 ml. of methanol on 2 g. of $CuCr_2O_4$ catalyst at 100 atmospheres and 140°. The mixture is cooled, filtered, and evaporated, thus producing 2-(2-xanthenyl)-propanol, m.p. 86°–89°.

EXAMPLE 22

A solution of 2.54 g. of 2-(2-xanthenyl)-propionic acid in 20 ml. of absolute THF is added dropwise to a mixture of 0.57 g. of $LiAlH_4$ in 20 ml. of absolute THF. The mixture is refluxed for 8 hours, 2 ml. of water in 3 ml. of THF, as well as 4 ml. of 25% sodium hydroxide solution are added thereto, the mixture is decanted and the residue washed with ether. After the drying, filtration, and evaporation of the combined organic phases, 2-(2-xanthenyl)-propanol is obtained, m.p. 86°–89°.

EXAMPLE 23

2.38 g. of 2-(2-xanthenyl)-propanal is dissolved in 10 ml. of ethanol and added dropwise to a solution of 0.6 g. of $NaBH_4$ in 15 ml. of ethanol. The mixture is agitated for 2 hours at 20° and worked up as usual, thus producing 2-(2-xanthenyl)-propanol, m.p. 86–89°.

EXAMPLE 24

2.4 g. of 2-(2-xanthenyl)-propylamine (obtainable from 2-(2-xanthenyl)-propionamide with $LiAlH_4$) is dissolved in 50 ml. of 15% aqueous acetic acid and mixed, under ice cooling, with a solution of 1 g. of $NaNO_2$ in 5 ml. of water. The mixture is heated for 1 hour to 80°, worked up as usual, and chromatographic purification on silica gel yields 2-(2-xanthenyl)-propanol, m.p. 86°–89°.

EXAMPLE 25

3 g. of 1-bromo-(2-xanthenyl)-propane is dissolved in 20 ml. of DMF, mixed with 3 g. of anhydrous potassium acetate, and stirred for 3 hours at 60°. The mixture is worked up as usual, thus obtaining 2-(2-xanthenyl)-propyl acetate, m.p. 62°–64°. Additionally, a small amount of 2-(2-xanthenyl)-propene is produced.

EXAMPLE 26

2 g. of 2-(2-xanthenyl)-propyl benzyl ether (obtainable from 1-bromo-2-(2-xanthenyl)-propane and sodium benzylate) is dissolved in 25 ml. of methanol and hydrogenated on 0.2 g. of 5% Pd-C catalyst at 20° until the absorption of hydrogen is terminated. The mixture is filtered off and evaporated, thus obtaining 2-(2-xanthenyl)-propanol, m.p. 86°–89°.

EXAMPLE 27

3 g. of 2-[3-(o-hydroxybenzyl)-4-hydroxyphenyl]-propyl acetate is heated with 0.7 g. of $ZnCl_2$ for 2 hours to 170°. After working up the reaction mixture as usual, 2-(2-xanthenyl)-propyl acetate is obtained, m.p. 62°–64°.

EXAMPLE 28

10 g. of 2-(9-oxo-2-xanthenyl)-propanol is hydrogenated in 300 ml. of ethanol in the presence of 0.5 g. of 5% Pd-C under a pressure of 3 atmospheres and at 20° until absorption of the theoretical amount of H. After filtration and concentration, 2-(2-xanthenyl)-propanol is obtained, m.p. 86°–89°.

EXAMPLE 29

A mixture of 10 g. of 2-(9-oxo-2-xanthenyl)-propanol, 12 g. of amalgamized zinc, 15 ml. of water, 40 ml. of concentrated hydrochloric acid, and 20 ml. of toluene is refluxed for 48 hours. At 8 hour intervals, another 10 ml. of concentrated hydrochloric acid is added. After filtration over active carbon and removal of the solvent mixture by evaporation, 2-(2-xanthenyl)-propanol is obtained, m.p. 86°–89°.

EXAMPLE 30

10 g. of 2-(9-oxo-2-xanthenyl)-propanol, 20 g. of amalgamized zinc, 20 ml. of ethanol, and 50 ml. of concentrated hydrochloric acid are refluxed for 30 hours. After 8 and 16 hours, 5 ml. portions of concentrated hydrochloric acid are added. After working up the mixture as usual, 2-(2-xanthenyl)-propanol is obtained, m.p. 86°–89°.

EXAMPLE 31

10 g. of 2-(9-oxo-2-xanthenyl)-propanol is heated with 5.5 g. of zinc dust for 1 hour to 220°. Thereafter, the mixture is distilled under reduced pressure, thus producing 2-(2-xanthenyl)-propanol, m.p. 86–89°.

EXAMPLE 32

10 g. of 2-(9-oxo-2-xanthenyl)-propanol is heated with 35 g. of hydrazine hydrate in an autoclave for 6 hours to 200°. After cooling, the mixture is poured into water and worked up as usual, thus producing 2-(2-xanthenyl)-propanol, m.p. 86°–89°.

EXAMPLE 33

25.2 g. of 2-(9-oxo-2-xanthenyl)-propanal is dissolved in 100 ml. of n-butanol and mixed with 6.4 g. of anhydrous hydrazine. The mixture is heated for 30 minutes on a water bath, the n-butanol is distilled off, the residue mixed with 300 ml. of toluene and 20 g. of potassium tert.-butylate, and the mixture is refluxed until the evolution of gas has ceased. After working up the mixture as usual, 2-(2-xanthenyl)-propanol is obtained, m.p. 86°–89°.

EXAMPLE 34

10 g. of 2-(9-oxo-2-xanthenyl)-propanol is refluxed with 1 g. of red phosphorus in 50 ml. of hydriodic acid (b.p. 127°) for 4 hours. After the excess hydrogen iodide has been distilled off, 2-(2-xanthenyl)-propanol is obtained, m.p. 86°–89°.

EXAMPLE 35

A mixture of 10 g. of 2-(9-hydroxy-2-xanthenyl)-propanol, 45 ml. of acetic acid, and 20 g. of concentrated hydriodic acid is refluxed for 3 minutes. After removal of the solvent by evaporation, 2-(2-xanthenyl)-propanol is obtained, m.p. 86°–89°.

EXAMPLE 36

2.56 g. of 2-[3-(o-aminobenzyl)-4-aminophenyl]-propanol is diazotized in dilute hydrochloric acid with 1.4 g. of NaNO$_2$. The mixture is allowed to stand for 15 minutes and then heated on a water bath until the evolution of nitrogen has ceased. As an intermediate product, 2-[3-(o-hydroxybenzyl)-4-hydroxyphenyl]-propanol is produced which is not isolated. After working up the mixture as usual, 2-(2-xanthenyl)-propanol is obtained, m.p. 86°–89°.

EXAMPLE 37

A mixture of 2.8 g. of 2-[3-(o-hydroxybenzyl)-4-chlorophenyl]-propanol, 0.6 g. of KOH, and 0.1 g. of Cu powder is heated for 5 hours to 190°. After cooling and working up the mixture as usual, 2-(2-xanthenyl)-propanol is obtained, m.p. 86°–89°.

2-[3-(o-Chlorobenzyl)-4-hydroxyphenyl]-propanol reacts analogously.

EXAMPLE 38

15.3 g. of 2-[4-(2-aminomethylphenoxy)-phenyl]-propanol is dissolved in 120 ml. of water and 40 ml of concentrated hydrochloric acid and diazotized at 0°–5° with 4.2 g. of NaNO$_2$ in 15 ml. of water. The thus-obtained diazonium salt solution is poured into 200 ml. of hot 50% H$_2$SO$_4$ and is further heated until the evolution of nitrogen has stopped. After working up the mixture as usual, 2-(2-xanthenyl)-propanol is obtained, m.p. 86°–89°.

The following examples relate to pharmaceutical preparations containing xanthene derivatives of general Formula I:

EXAMPLE A

Tablets

A mixture consisting of 200 kg. of 2-(2-xanthenyl)-propanol, 600 kg. of lactose, 160 kg. of corn starch, 20 kg. of talc, and 20 kg. of magnesium stearate is compressed into tablets by the conventional method, so that each tablet contains 200 mg. of the effective agent.

EXAMPLE B

Dragees

Tablets are pressed analogously to Example A and are then coated in the usual manner with an envelope consisting of sugar, corn starch, talc, and tragacanth.

Analogously, tablets and dragees can be obtained which contain one or more of the other effective agents of Formula I.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A xanthene of the formula
Z-CHR$_1$R$_2$
wherein Z is 2-xanthenyl or 2-xanthenyl substituted at the 1-, 3-, 4-, 5-, 6-, 7- or 8-position by F, Cl or Br, R$_1$ is CH$_2$OH or CH$_2$OAc, wherein Ac is alkanoyl of 2–4 carbon atoms and R$_2$ is alkyl of 1-4 carbon atoms.

2. A compound of claim 1 wherein Z is unsubstituted 2-xanthenyl.
3. A compound of claim 1 wherein $R_1$ is $CH_2OH$.
4. A compound of claim 1 wherein $R_2$ is $CH_3$ or $C_2H_5$.
5. A compound of claim 4 wherein $R_2$ is $CH_3$.
6. A compound of claim 1 wherein Z is 2-xanthenyl substituted by Cl.
7. A compound of claim 1 wherein $R_1$ is $CH_2OOCCH_3$.
8. The compound of claim 1, 2-(2-xanthenyl)-propanol.
9. The compound of claim 1, 2-(2-xanthenyl)-propyl acetate.

* * * * *